(12) United States Patent
Palmer et al.

(10) Patent No.: US 6,660,021 B1
(45) Date of Patent: Dec. 9, 2003

(54) INTRAVASCULAR DEVICE AND SYSTEM

(75) Inventors: Olin Palmer, Mountain View, CA (US); Christopher T. Shen, Stanford, CA (US); Robert LaDuca, Davenport, CA (US); Larry Voss, Vancouver (CA); Saypin Phonthalasa, San Francisco, CA (US); John E. Papp, Temecula, CA (US); Stephen A. Morales, Santa Clara, CA (US); Coeta K. Peloquin, Fallbrook, CA (US); Charles R. Peterson, Murrieta, CA (US); Anuja H. Patel, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/919,507

(22) Filed: Jul. 31, 2001

Related U.S. Application Data

(63) Continuation-in-part of application No. 09/469,431, filed on Dec. 23, 1999, now Pat. No. 6,402,771.

(51) Int. Cl.[7] .............................................. A61M 29/00
(52) U.S. Cl. ....................................................... 606/200
(58) Field of Search ................................. 606/200, 113, 606/114, 127, 159

(56) References Cited

U.S. PATENT DOCUMENTS

| 4,425,908 | A | * | 1/1984 | Simon ........................ 606/200 |
| 5,064,428 | A | | 11/1991 | Cope et al. |
| 5,102,415 | A | | 4/1992 | Guenther et al. |
| 5,329,942 | A | | 7/1994 | Gunther et al. |
| 5,350,398 | A | | 9/1994 | Pavcnik et al. |
| 5,601,595 | A | | 2/1997 | Smith |
| 5,720,764 | A | | 2/1998 | Naderlinger |
| 5,792,145 | A | | 8/1998 | Bates et al. |
| 5,792,157 | A | | 8/1998 | Mische et al. |
| 5,810,874 | A | | 9/1998 | Lefebvre |
| 5,814,064 | A | | 9/1998 | Daniel et al. |
| 5,910,154 | A | | 6/1999 | Tsugita et al. |
| 5,941,869 | A | | 8/1999 | Patterson et al. |
| 5,941,896 | A | | 8/1999 | Kerr |
| 5,954,745 | A | | 9/1999 | Gertler et al. |
| 5,968,071 | A | | 10/1999 | Chevillon et al. |
| 6,152,946 | A | | 11/2000 | Broome et al. |
| 6,171,327 | B1 | | 1/2001 | Daniel et al. |
| 6,179,859 | B1 | | 1/2001 | Bates et al. |
| 6,179,861 | B1 | | 1/2001 | Khosravi et al. |
| 6,214,025 | B1 | | 4/2001 | Thistle et al. |
| 6,383,205 | B1 | * | 5/2002 | Samson et al. ............. 606/200 |

FOREIGN PATENT DOCUMENTS

| FR | 2 652 267 A1 | 3/1991 |
| WO | WO 99/65417 | 12/1999 |
| WO | WO 01/08595 | 2/2001 |
| WO | WO 01/32254 A1 | 5/2001 |
| WO | WO 01/45590 A2 | 6/2001 |
| WO | WO 01/52768 A1 | 7/2001 |

* cited by examiner

Primary Examiner—Kevin T. Truong
(74) Attorney, Agent, or Firm—Fulwider Patton Lee & Utecht, LLP

(57) ABSTRACT

A device for use in capturing or collecting debris found in blood vessels or other body lumens. The devices can be fabricated from a tube and include longitudinally and circumferentially extending members. The device can further embody structure that provides enhanced radial opening and angular resistance to collapse and structure for absorbing or modifying forces applied thereto by an operator.

7 Claims, 13 Drawing Sheets

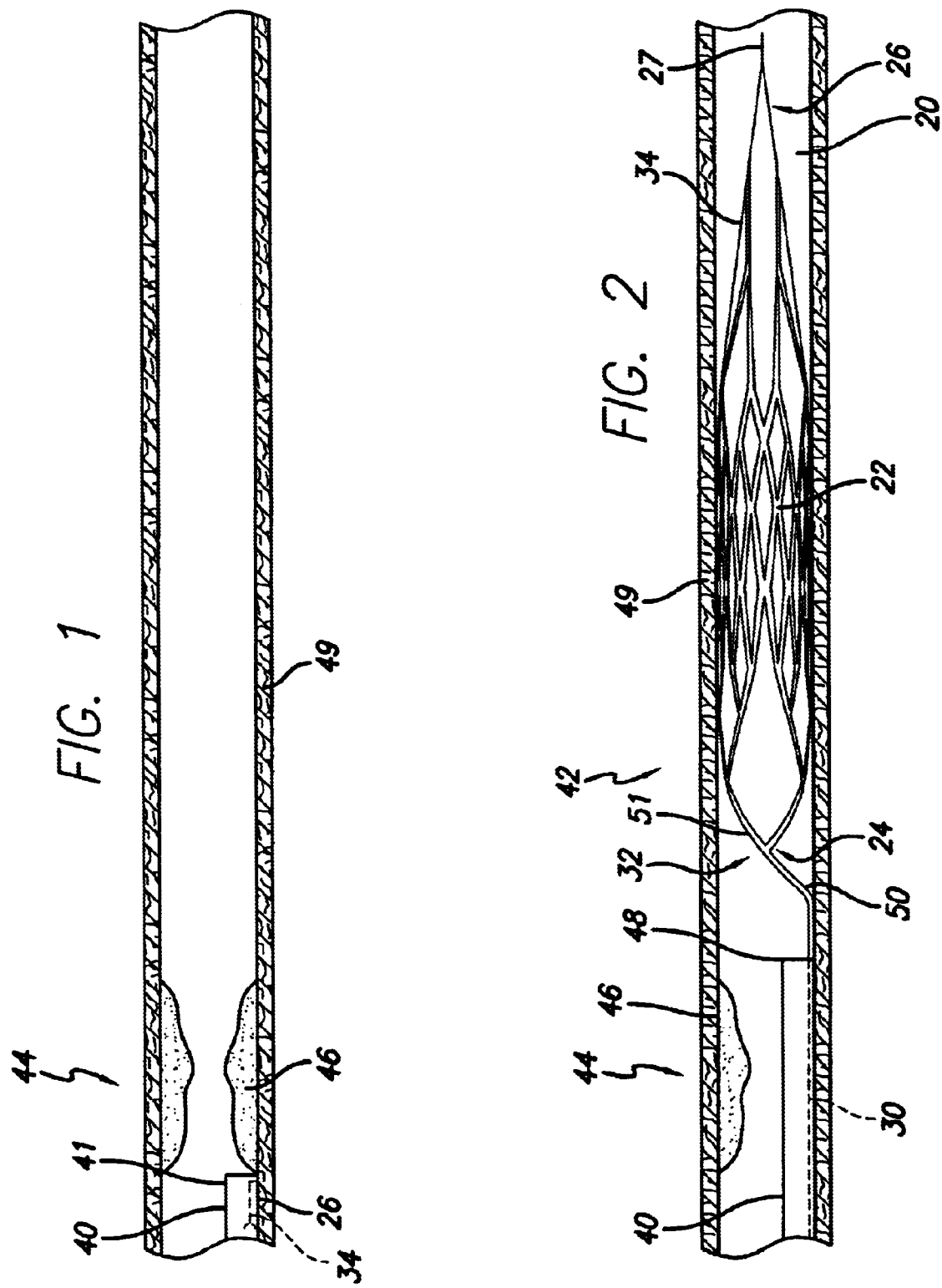

FIG. 31
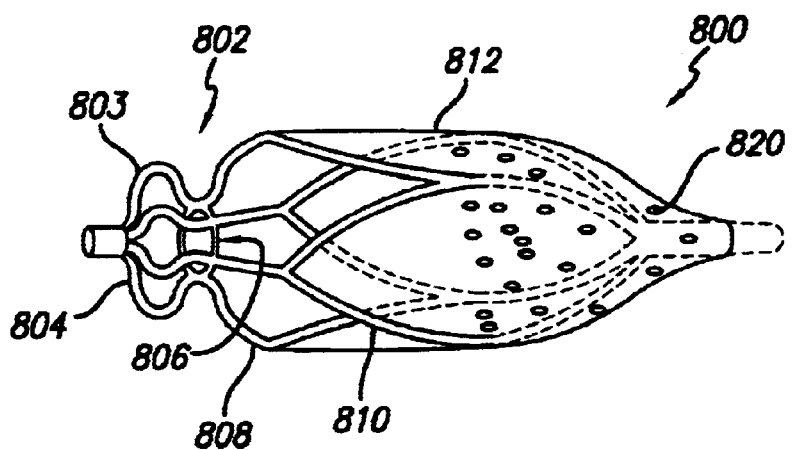
FIG. 32
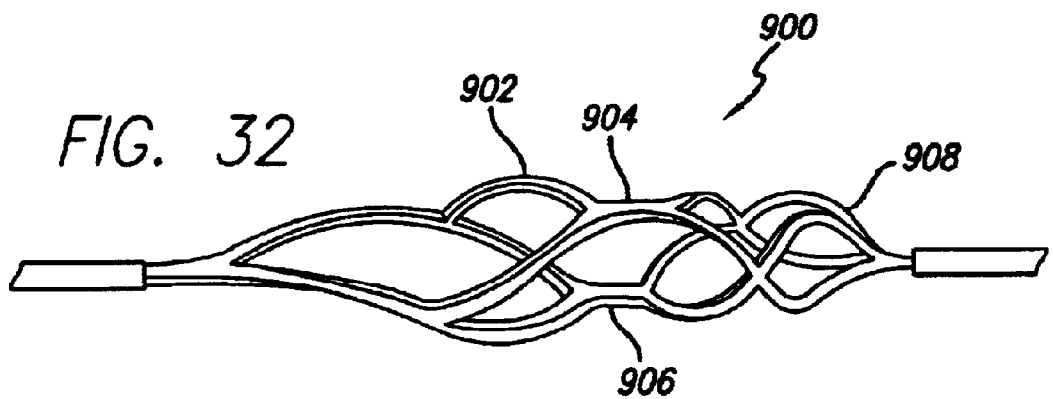
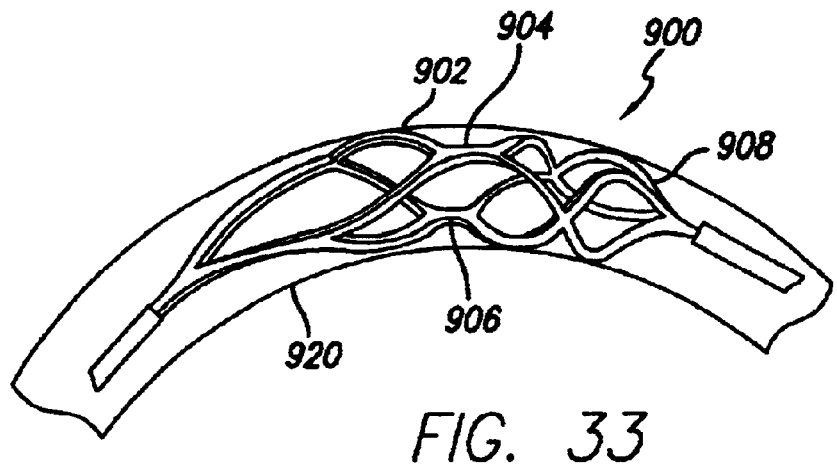
FIG. 33

INTRAVASCULAR DEVICE AND SYSTEM

This application is a continuation-in-part of U.S. application Ser. No. 09/469,431, filed Dec. 23, 1999 now U.S. Pat. No. 6,402,771.

BACKGROUND OF THE INVENTION

The present invention relates generally to intravascular devices and systems and more particularly, devices which can be used to capture embolic material or thrombi found in blood vessels.

The intravascular devices and systems of the present invention are particularly useful when performing balloon angioplasty, stenting procedures, laser angioplasty or atherectomy in critical vessels where the release of embolic debris into the bloodstream can occlude the flow of oxygenated blood to the brain or other vital organs, which can cause devastating consequences to the patient. The disclosed devices are also suited for the removal of clots obstructing, or partially obstructing blood vessels. The device is also suitable for removal of misplaced coils or other foreign material. While the devices and systems of the present invention are particularly useful in the cerebral vasculature and neurovasculature, the invention can be used in conjunction with any vascular interventional procedure in which there is an embolic risk. Additionally, it can be used in any region of the body where removal of debris or foreign material is indicated.

A variety of non-surgical interventional procedures have been developed over the years for opening stenosed or occluded blood vessels in a patient caused by the build up of plaque or other substances on the wall of the blood vessel. Such procedures usually involve the remote introduction of the interventional device into the lumen of the artery, usually through a catheter. In typical carotid PTA procedures, a guiding catheter or sheath is percutaneously introduced into the cardiovascular system of a patient through the femoral artery and advanced, for example, through the vasculature until the distal end of the guiding catheter is in the common carotid artery. A guidewire and a dilatation catheter having a balloon on the distal end are introduced through the guiding catheter with the guidewire sliding within the dilatation catheter. The guidewire is first advanced out of the guiding catheter into the patient's carotid vasculature and is directed across the arterial lesion. The dilatation catheter is subsequently advanced over the previously advanced guidewire until the dilatation balloon is properly positioned across the arterial lesion. Once in position across the lesion, the expandable balloon is inflated to a predetermined size with a radiopaque liquid at relatively high pressures to radially compress the atherosclerotic plaque of the lesion against the inside of the artery wall and thereby dilate the lumen of the artery. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty.

Another procedure is laser angioplasty which utilizes a laser to ablate the stenosis by super heating and vaporizing the deposited plaque. Atherectomy is yet another method of treating a stenosed blood vessel in which cutting blades are rotated to shave the deposited plaque from the arterial wall. A vacuum catheter is usually used to capture the shaved plaque or thrombus from the blood stream during this procedure.

In the procedures of the kind referenced above, abrupt reclosure may occur or restenosis of the artery may develop over time, which may require another angioplasty procedure, a surgical bypass operation, or some other method of repairing or strengthening the area. To reduce the likelihood of the occurrence of abrupt reclosure and to strengthen the area, a physician can implant an intravascular prosthesis for maintaining vascular patency, commonly known as a stent, inside the artery across the lesion. The stent is crimped tightly onto the balloon portion of the catheter and transported in its delivery diameter through the patient's vasculature. At the deployment site, the stent is expanded to a larger diameter, often by inflating the balloon portion of the catheter.

Prior art stents typically fall into two general categories of construction. A first type of stent is expandable upon application of a controlled force, as described above, through the inflation of the balloon portion of a dilatation catheter which, upon inflation of the balloon or other expansion means, expands the compressed stent to a larger diameter to be left in place within the artery at the target site. A second type of stent is a self-expanding stent formed from, for example, shape memory metals or super-elastic nickel-titanum (NiTi) alloys, which will automatically expand from a compressed state when the stent is advanced out of the distal end of the delivery catheter into the body lumen. Such stents manufactured from expandable heat sensitive materials allow for phase transformations of the material to occur, resulting in the expansion and contraction of the stent.

The above minimally invasive interventional procedures, when successful, avoid the necessity of major surgical operations. However, there is one common problem which can become associated with all of these types of procedures, namely, the potential release of embolic debris into the bloodstream that can occlude distal vasculature and cause significant health problems to the patient. For example, during deployment of a stent, it is possible that the metal struts of the stent can cut into the stenosis and shear off pieces of plaque which become embolic debris that can travel downstream and lodge somewhere in the patient's vascular system. Pieces of plaque material can sometimes dislodge from the stenosis during a balloon angioplasty procedure and become released into the bloodstream. Additionally, while complete vaporization of plaque is the intended goal during a laser angioplasty procedure, quite often particles are not fully vaporized and thus enter the bloodstream. Likewise, not all of the emboli created during an atherectomy procedure may be drawn into the vacuum catheter and, as a result, enter the bloodstream as well.

When any of the above-described procedures are performed in the carotid arteries, cerebral vasculature, or neurovasculature, the release of emboli into the circulatory system can be extremely dangerous and sometimes fatal to the patient. Naturally occurring debris can also be highly dangerous to a patient. That is, debris which travels through the blood vessel as a natural result of bodily functions and not as a result of an intervention procedure. Debris that is carried by the bloodstream to distal vessels of the brain can cause these cerebral vessels to occlude, resulting in a stroke, and in some cases, death. Therefore, although cerebral percutaneous transluminal angioplasty has been performed in the past, the number of procedures performed has been limited due to the justifiable fear of causing an embolic stroke should embolic debris enter the bloodstream and block vital downstream blood passages.

Medical devices have been developed to attempt to deal with the problem created when debris or fragments that naturally occur or that enter the circulatory system following vessel treatment utilizing any one of the above-identified procedures. One approach which has been attempted is the cutting of any debris into minute sizes which pose little chance of becoming occluded in major vessels within the patient's vasculature. However, it is often difficult to control the size of the fragments which are formed, and the potential risk of vessel occlusion still exists, making such a procedure in the carotid arteries a high-risk proposition.

In addition, the retrieval of fragmented clot may be incomplete, also resulting in emboli and distal occlusions, and further, access through tortuous lumens may prove difficult. Laser-based disruption devices employ the photo-acoustic effect to fragment clot. Local disruption may open up a proximal occlusion but also may cause significant distal emboli.

Other techniques which have been developed to address the problem of removing embolic debris include the use of catheters with a vacuum source which provides temporary suction to remove embolic debris from the bloodstream. However, as mentioned above, there have been complications with such systems since the vacuum catheter may not always remove all of the embolic material from the bloodstream, and a powerful suction could otherwise cause problems to the patient's vasculature. Other techniques which have had some limited success include the placement of a filter or trap downstream from the treatment site to capture embolic debris before it reaches the smaller blood vessels downstream. However, there have been problems associated with conventional filtering systems as well. In particular, certain previously developed filtering devices do not optimize the area for embolic collection. That is, conventional filtering devices may not present a collection device that spans the entity of the vessel or it may include supporting structure that itself impedes emboli collection. Certain other devices do not embody sufficient angular resistance to collapse or do not expand to seat evenly against the vessel wall allowing emboli to pass between the device and the vessel wall.

Moreover, thrombectomy and foreign matter removal devices have been disclosed in the art. However, in addition suffering from the same disadvantages as certain conventional filter devices, such devices have been found to have structures which are either highly complex such as with multiple components or highly convoluted geometry or lacking in sufficient or effective expansion and retraction capabilities. Disadvantages associated with the devices having highly complex structure such as with multiple components or highly convoluted geometry include difficulty in manufacturability as well as use in conjunction with micro-catheters.

Other devices with less coverage can pull through clots due in part to the lack of experience in using the same or otherwise lack of an expanded profile that is adequate to capture clots or foreign bodies.

Furthermore, in current interventional radiology practice, the need arises to remove a variety of objects from intraluminal spaces. Among these are embolic coils, guidewire tips, distal catheter segments, thrombus and other vascular emboli, few of which can be readily removed with current devices.

Thrombo-embolic materials can be friable, amorphous, and/or lubricious in nature, contributing to this difficulty. Most current therapies rely on grasping, fragmenting, or dissolving the blood-based obstructions. Among the grasping devices are the loop snares and the wire basket snares. These devices may have limited effectiveness, due in part to the lack of encapsulation. Objects are difficult to grasp within these devices, and friable objects, e.g. blood-based blockages, tend to fragment when grasped or pulled, introducing multiple smaller emboli.

Lytic drugs are also used to dissolve blood-based obstructions. These typically have the disadvantages of lengthy treatment/infusion times to remove the obstruction (>3 hrs.), production of emboli, and the potential for systemic iatrogenic bleeding as a side effect of the drug usage. Also, these drugs are not typically effective in removing obstructions that are not blood-based.

What has been needed is a reliable intravascular device and system for use when treating blood vessels. The devices should be capable of capturing any naturally occurring embolic debris or that which may be released into the bloodstream during an interventional treatment, and safely containing the debris until the device is removed from the patient's vasculature. The devices should embody an expanded profile that presents a consistent radial opening that completely occupies the vessel at the repair site as well as structure for effectively resisting collapse. Moreover, such devices should be relatively easy to deploy and remove from the patient's vasculature also should be capable of being used in narrow and very distal vasculature such the cerebral vasculature. The following invention addresses these needs.

SUMMARY OF THE INVENTION

Briefly and in general terms, the present invention is directed towards devices for removing undesired material or objects and maintaining or restoring patency of blood vessels or other luminal spaces. The devices of the present invention include structure that is linked or embodies a monolithic framework of thin struts which are radially expansible.

In one aspect of the invention, the devices include struts (members run both generally longitudinally and generally circumferentially) with very small widths and thicknesses that can be configured into rings (circumferential members) with very small widths and thicknesses but large expansion ratios. The body of the devices is defined by a plurality of openings bounded by generally longitudinally and generally circumferentially extending members. A proximally extending member is attached to an elongate wire and the assembly is contemplated to be used in conjunction with a generally tubular delivery catheter.

Overall, the intent of the invention is to provide a structure that has the capacity to engage and retain naturally occurring or foreign bodies while having a minimal profile that can traverse easily and repeatably through a standard catheter across tortuous anatomy. The device embodies superior flexibility to be deployed and retrieved consistently across difficult anatomy while being able to retain captured material. The diameter of the device is heat-set to a predetermined size. It is envisioned that there be a family of devices that have varying strut lengths, thicknesses, flexibility, and diameters as deemed appropriate for the specific type of vascular or non-vascular setting for which the device is to be used.

In a presently preferred embodiment, the devices are self-expanding and include a midsection that forms a generally tubular profile. The devices can assume a number of forms. In one presently contemplated aspect, the device of the present invention embodies first and second end portions, a pair of longitudinally spaced rings and a midsection defined by helically extending members. In another aspect, the intravascular device has a midsection defined by generally parallel longitudinally extending members. In other aspects, the device includes a single convoluted ring or alternatively a body defined by a truncated stirrup-like structure. In yet another embodiment, the device has a midsection including almond-shaped apertures as viewed perpendicular to the axis of the device.

In other aspects, the devices of the present invention are contemplated for use as protection devices which are deployed in the region of a repair site during the performance of an interventional procedure. Such protection devices can include a filtering portion intended to facilitate the capture of debris created during the interventional procedure. Structure is additionally provided to aid the apposition of the protection device against walls defining the body lumen into which the device is deployed. Structure can also be provided to allow the body of the protection device to rotate independently of an elongate member attached to the body or which absorbs or modifies forces applied to the device via the elongate member being manipulated by an operator.

Moreover, the present invention embodies a tip for an endovascular device including an atraumatic soft tip for preventing damage to tissue and facilitates advanceability. The tip can further includes multiple layers of coiled material to enhance these objectives as well as to provide stiffness variations. In certain embodiments, the distal end portion of devices of the present invention are equipped with a tapered section which provides the devices with desired transitioning in flexibility.

These and other objects and advantages of the invention will become apparent from the following more detailed description, when taken in conjunction with the accompanying drawings of illustrative embodiments.

BRIEF DESCRIPTION OF THE DRAWINGS

FIG. 1 is a side view, partially in cross-section, of a vessel partially occluded by a stenosis and a distal portion of a delivery catheter and intravascular snare assembly of the present invention positioned proximate the debris;

FIG. 2 is a side view, partially in cross-section, of the intravascular snare of FIG. 1 deployed within the vessel;

FIG. 31 is a perspective view of a seventh embodiment of a protection device;

FIG. 32 is a perspective view of an eighth embodiment of a protection device; and FIG. 33 is a partial cross-sectional view, depicting the protection device of FIG. 32 deployed within a body lumen.

DETAILED DESCRIPTION OF THE PREFERRED EMBODIMENTS

Figure 3:
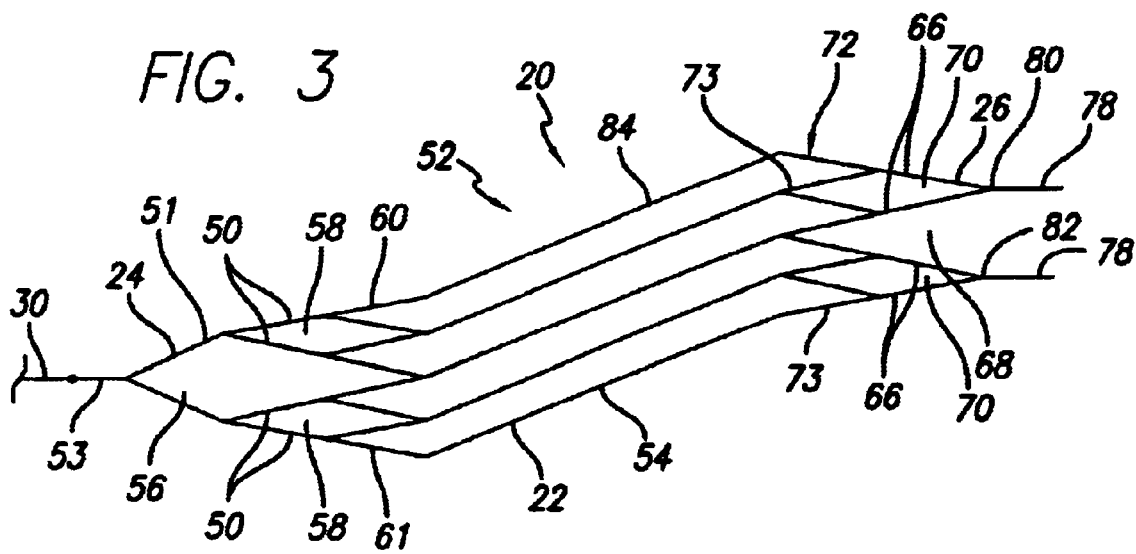
FIG. 3 is a plan view depicting an unrolled pattern of an intravascular snare of the present invention.

Referring now to the drawings, and in particular FIGS. 1 and 2, there is shown a snare device of the present invention. The snare device 20 is adapted to provide more consistent and improved radial opening as well as enhanced angular resistance to collapse. Moreover, the snare device 20 of the present invention is configured to facilitate the maintenance of clearance in its interior space along its length allowing the material or objects to enter and be captured. Furthermore, since it is contemplated that the snare device 20 be manufactured from a tubular member to form elements with very small widths and thicknesses, the device is thus more easily packed to a relatively smaller diameter and inherently embodies high longitudinal flexibility.

The snare device 20 (FIG. 2) of the present invention includes a body 22 having a proximal end portion 24 and a distal end portion 26. The proximal end portion 24 is intended to be affixed to a terminal end portion of an elongate member 30 (i.e., wire; described in more detail below). In a presently preferred embodiment, the body 22 of the snare device 20 is generally tubular with a proximally directed opening 32 and a generally closed terminal end 34 to thereby form a basket for receiving embolus, stones, thrombus and foreign bodies found in vasculature or other body cavities.

The snare device 20 for intravascular uses is contemplated to be used in conjunction with a generally tubular delivery catheter 40, such as a microcatheter. Additionally, it is contemplated that a conventional guide catheter (not shown) be used in combination with the delivery catheter 40 loaded with a snare device 20. The guide catheter is employed to provide a guide within a patient's vasculature through which the delivery catheter 40 is inserted. A proximal end of the guide may include a "Y" adapter or hemostatic valve fitted with sealing, hemostatic valves. The snare device 20 is intended to be self-expandable, however, it is possible to employ an expandable member such as a balloon catheter (not shown) to radially expand a snare device that is not self-expandable, but rather must be deformed to assume an expanded configuration.

In use, the body 22 of a snare device 20 is inserted proximally in a compressed configuration coaxially within an internal bore of the generally tubular delivery catheter 20. The longitudinally extending elongate member 30 which is attached to the proximal end 24 of the body 22, is likewise coaxially received within the delivery catheter 40. Both the body 22 and elongate member 30 are slidable within the delivery catheter 40 and accordingly, the delivery catheter 40 and the snare device 20 can be displaced longitudinally with respect to each other.

A typical procedure will now be described. In order to restore patency in a vessel, the snare device/delivery catheter assembly 42 is introduced into a patient's vasculature using conventional means such as the Seldinger technique. Sometimes, a cutdown is made to gain access to the patient's vasculature. Using standard endovascular techniques, the emboli in the vasculature is located. The delivery catheter 40 and guidewire (not shown) are navigated past the emboli. If angiographic mapping was not possible prior to crossing the treatment area, contrast is injected distal to the occlusion to map the distal vessels. The tip 26 of the delivery catheter 40 is positioned one body length or slightly more beyond the emboli. The guidewire is removed and the snare device 20 is loaded through a rear hub (not shown) of the delivery catheter 20 with the assistance of a conventional introducer sheath (not shown). The snare device 20 is advanced 30–40 cm and the introducer sheath is then removed.

Next, the snare device 20 is advanced until the tip 26 of the basket is positioned at the distal end of the delivery catheter 40. The snare device 20 is held in place by the operator holding the elongate member 30 still while the catheter 40 is retracted to allow the device to expand. Holding the snare device 20 in place, the catheter 40 is pulled back until it is proximal to the emboli 46. The entire system is drawn back holding relative positions between the snare device 20 and the catheter 40, allowing the emboli 40 to enter the snare device 20. This step can be assisted with a "stuttering" technique where the snare device 20 is drawn out a small amount, perhaps 2 mm, then the elongate member 30 is advanced back perhaps 1 mm to flare the mouth of the snare device 20, assisting clot entry. Then the system is drawn out another 1 mm. This is repeated until the device 20 has traversed a distance about its own length.

To reduce the risk of losing the material contained in the basket or device, blood flow control may be used during extraction. For example, a guiding catheter with a flow control device such as an elastomeric balloon at the distal tip may be employed to slow or stop blood flow past the device during retrieval.

If the emboli is foreign in origin, such as a coil, the basket can be moved back and forth past the coil in an iterative attempt to engage the coil in the struts of the basket. When this has occurred, the catheter 40 can be advanced causing the basket to collapse and pinch the coil, locking it into one of the openings of the basket. If the emboli is not radiopaque, its position may be checked by a contrast injection and noting a filling defect. Also, the radiopaque tip 26 of snare device 20 can be observed under fluoroscopy during this process. A pulsing motion can indicate restored flow.

The system 42 is then drawn back until the distal end of a proximal device marker coil (described below) is at the tip of the guide. At this point, a large syringe, perhaps 60 cc, is attached to the guide catheter at the rotating hemostatic valve on the hub. The guide catheter is aspirated as the snare device 20 and emboli 46 are drawn into the guide. Aspiration is maintained until the snare device 20 is fully into the rotating hemostatic valve of the guide catheter, but the snare device 20 is not yet drawn through the hemostatic valve. The rotating hemostatic valve is detached and removed with the snare device in it, allowing a moment of bleed back through the guide to flush any loose clot. Optionally, then a second rotating hemostatic valve is attached to prevent excessive bleed back. The guide is then flushed with saline and the entire procedure repeated as required to remove further emboli.

The manner in which the body portion 22 of the snare device 20 self-expands within vasculature and the resultant expansion profile provides a number of advantages. In particular, the body 22 expands to conform to the repair site 44. That is, the generally tubular profile of the body portion 22 substantially conforms to the walls defining the blood vessel 49. Alternatively, the snare device 20 can be sized such that upon full expansion it has a diameter smaller than the diameter of the vessel if desired. Moreover, the expansion of the body 22 facilitates the maintenance of clearance in its interior space along its length allowing the material or objects to enter and be captured and specifically provides a substantially unobstructed access to the proximally directed opening 32 to the body 22. Significantly, as the body 22 self-expands, members 50, 51 leading to the opening 32 to the body 22 are angled or oriented so as to be adjacent the walls defining the blood vessel 49 and are therefore substantially removed from the flow path to thereby provide an unobstructed opening 32 for emboli to enter and be captured.

In its expanded state, the snare device 20 is particularly well-suited to remove embolic or thrombotic debris 46 from the blood vessel 49. As stated, the snare device 20 can be withdrawn proximally so that the debris 46 can be captured by the body 22 of the snare device 20. Alternatively, a separate pusher mechanism (not shown) can be employed to push the debris 46 within the basket defined by the body portion 22. Once the debris has been captured, the snare device 20 and delivery catheter 40 can be removed from the patient's vasculature or the snare device 20 containing the debris 46 can first be pulled within the guide catheter (not shown) and then the assembly 42 removed from the target repair site 44. Also, just the proximal portion can be cinched down to lock the debris without being fully pulled into the delivery catheter 40.

It is to be understood, however, that thrombus or other blood-based material captured within the snare may be eliminated in a variety of ways. For example, the material may be drawn into the guide catheter with the aide of a vacuum applied to the guide catheter, and removed from the body. Also, these materials may be removed from the occluded vessel and allowed to dissolve under natural or induced lytic processes. Alternately, the material may be inserted into other vasculature more tolerant of occlusion and released.

Referring now to FIG. 3, there is shown one preferred pattern 52 of the snare device 20 of the present invention. As will be developed further below, it is contemplated that the snare pattern 52 be cut from a tubular member using a laser. Alternatively, the patterns can be made from a flat sheet of Nitinol and rolled into a tubular body. As best seen in its flattened or unrolled state, the snare pattern 52 composes a body 22 including proximal and distal end portions 24, 26, a midsection 54 and an elongate member 30 extending proximally from the proximal end portion 24.

Figure 8:
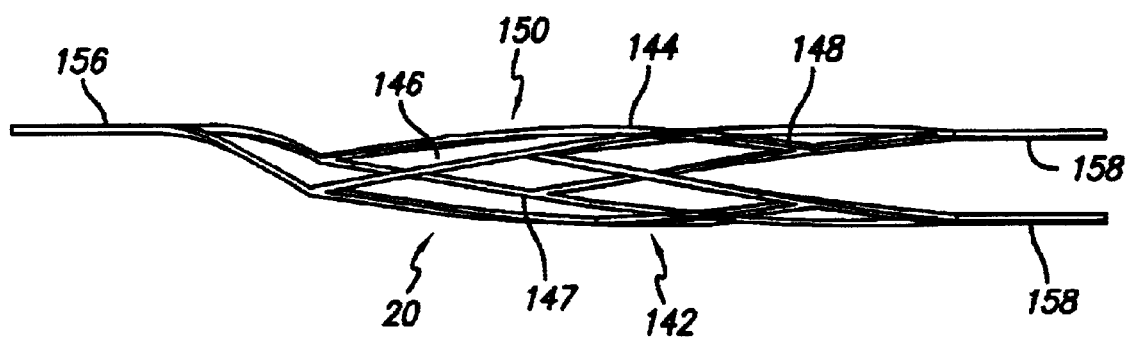
FIG. 8 is a perspective view of the embodiment depicted in FIG. 7.
Figure 9:
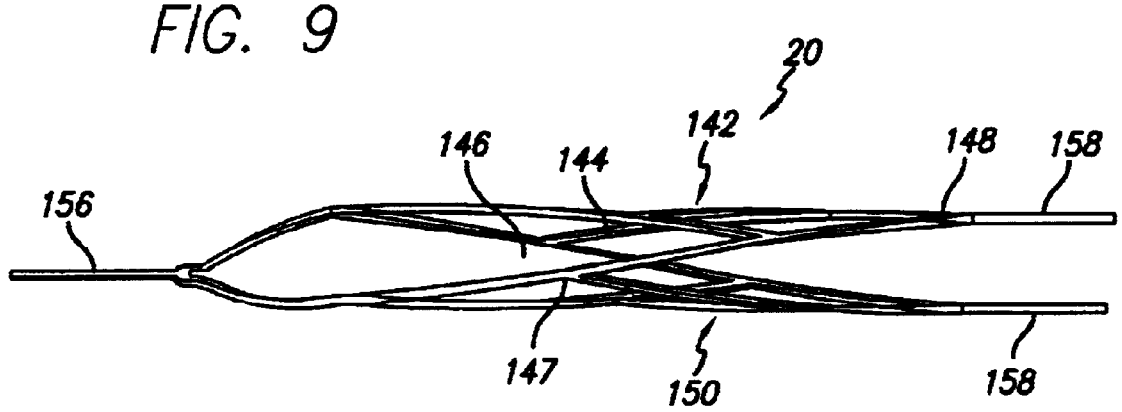
FIG. 9 is another perspective view of the embodiment depicted in FIG. 7.
Figure 10:
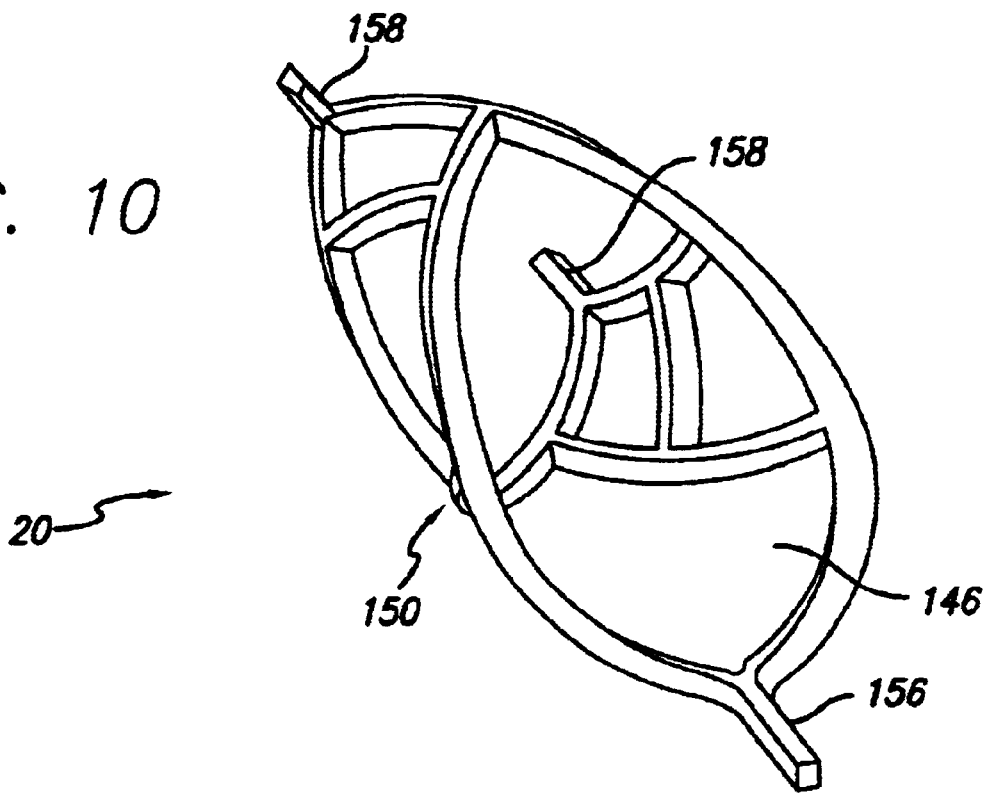
FIG. 10 is an end on view from a proximal end viewpoint of the embodiment depicted in FIG. 7.
Figure 11:
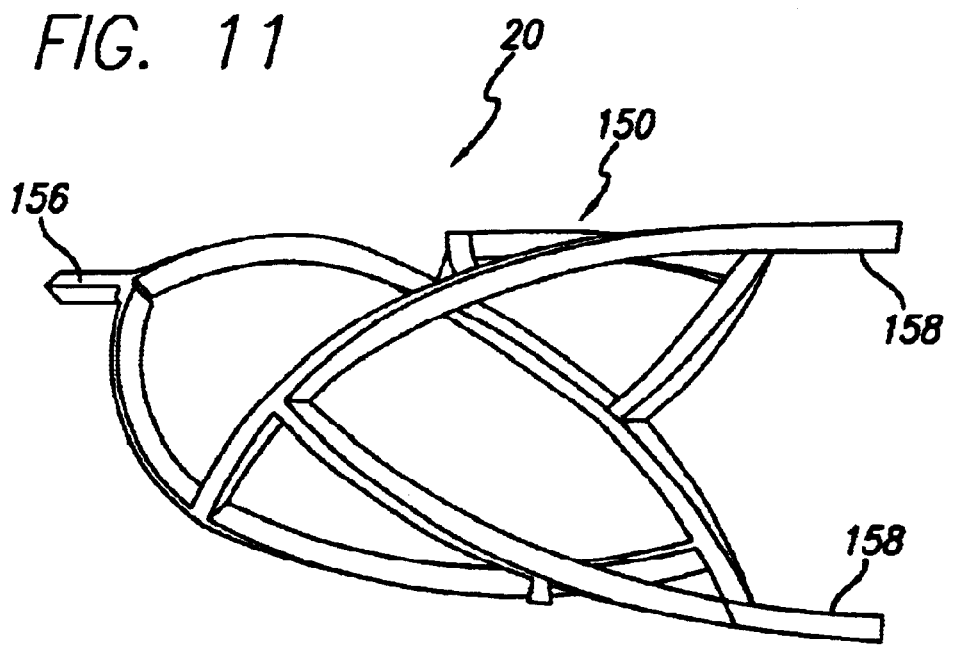
FIG. 11 is an end on view from a distal end viewpoint of the embodiment depicted in FIG. 7.

The proximal end portion 24 includes members or leashes 50 which lead to and aid in defining an opening to the body 22, when in its as cut configuration. The proximal end portion further embodies a pair of connectors 51 extending at an angle from the leashes 50 to thereby accomplish offsetting elongate member 70 from a central axis of the as cut tubular body 22 of snare device 20 as best seen in FIGS. 2 and 8. The connectors 51, in turn, converge to form a proximally directed tab 53 that is connected to the elongate member 30. The leashes 50 and connectors 51 define a centrally located, generally diamond-shaped aperture 56, having a first length, that is substantially sandwiched between two parallelogram-shaped, proximal apertures 58 having a relatively shorter second length. A proximal convoluted ring 60 defined by members 61 arranged in an alternating V-pattern located distally adjacent the proximal end portion 24. The ring 60 provides for optimal radial opening of the basket-like body 22.

The distal end portion 26 of the snare pattern 52 includes members or leashes 66 which define an open ended, distally directed triangle 68 sandwiched between a pair of two, parallelogram-shaped, distal apertures 70. A distal convoluted ring 72 defined by members 73 arranged in an alternating V-pattern located proximally adjacent the distal end portion 26. The ring 72 additionally provides for maximal radial opening of the body 27. Distally directed extensions 78 project, in a parallel fashion, from pairs of converging leashes 66.

The midsection 54 of the snare pattern 52 includes a plurality of generally parallel longitudinally extending members 84, each of which are joined at an angle and at one end, respectively, to the proximal ring 60. The other end of these members are joined at an angle to the distal ring 72.

In its as cut form, the terminal ends 80, 82 of the parallelogram-shaped, distal apertures 70 are joined together to form a substantially closed basket. This structure can be joined using soldering with or without employing a coil (described hereinbelow) that is wrapped about adjacent structures to form a soft tip. Distally directed extensions 78 may be trimmed to a desired length. The longitudinally extending members 84, while maintaining a parallel relationship, each define a helical pattern to thereby form a generally tubular midsection 54. The helical configuration provides flexibility around bends as well as good foreign body containment. The members 50 form a tapered opening to the generally tubular midsection 54 with the elongate member 30 extending proximally from a sidewall defined by the midsection 54. It is contemplated that the resultant tubular structure, in an undeformed state, includes a longitudinal axis that is generally parallel to both the elongate member 30 and the distally directed projections 78.

Figure 4:
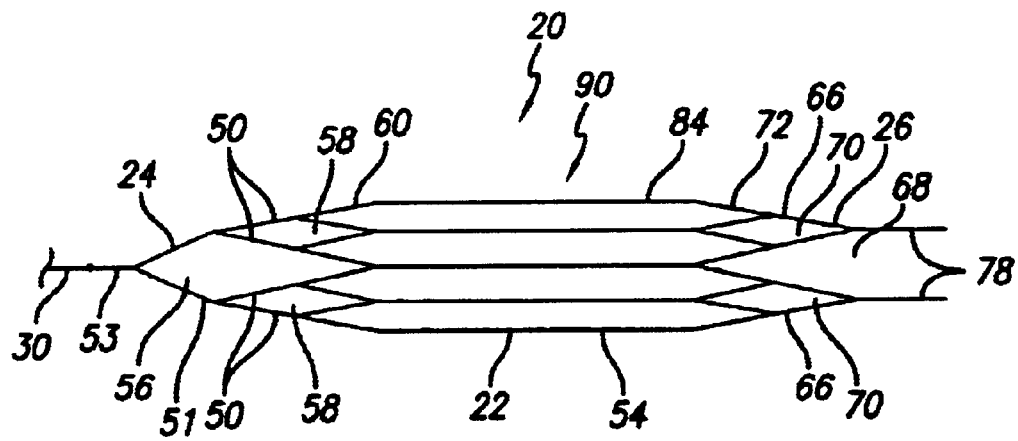
FIG. 4 is a plan view, depicting an unrolled pattern of an alternate embodiment of an intravascular snare of the present invention.

In an alternative embodiment of a snare pattern 90 (FIG. 4), the proximal end and distal end portions 24, 26 also include members 50, 51, 66 which define proximal and distal parallelogram-shaped apertures 58, 70 as well as a diamond-shaped aperture 56 and an open ended triangle 68. This second snare pattern 90 also similarly includes proximal and distal rings 60, 72 as well as distally directed extensions 78, each of which are joined to one of the distal parallelogram-shaped apertures 70. Moreover, the midsection 54 of the pattern 90 includes a plurality of parallel, longitudinally extending members 84 which are joined to the structure defining the proximal and distal end portions 24, 26. This embodiment differs from the first embodiment, however, in that the longitudinally extending members are not helically configured when the pattern 90 is in its as cut form. Rather, while defining a sidewall of a generally tubular midsection 54, each of the longitudinally extending members 84 are parallel to a longitudinal axis of the resultant tubular snare device 20. Being so arranged, the midsection 54 possesses the necessary flexibility to traverse sharp bends in anatomy as well as the capability of being packed into a small profile with minimal bulk.

Further, it is to be recognized that as with the first embodiment, a substantial closed-ended basket is formed by joining via conventional means the terminal ends 78 of the snare pattern 90. Additionally, a tapered opening to a generally tubular midsection 54 is provided by the proximal end portion 24 where the elongate member 30 extends proximally from a sidewall defined by the midsection 54.

Although each of the proximal and distal rings 60, 72 are shown as embodying a four crown design, fewer or more crowns are contemplated. Moreover, there need not be a leash 50, extending from each apex. It is necessary, however, that as with the ring design depicted, the modified pattern also result in rings that provide complete open deployment consistently and reliably. To wit, such rings do not fall back. That is, there is no angular deflection when the structure is pulled into a clot or foreign body.

Figure 5:
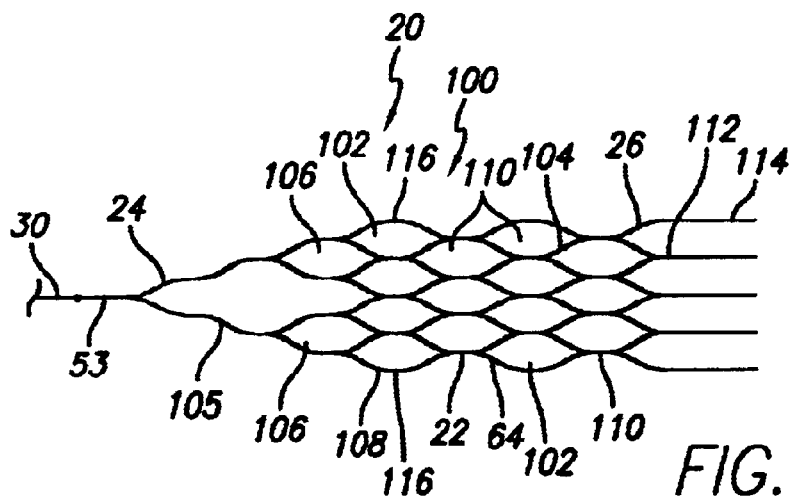
FIG. 5 is a plan view, depicting an unrolled pattern of a further alternate embodiment of an intravascular snare of the present invention.

Turning now to FIG. 5, in yet another embodiment of the snare device 20 of the present invention, a third snare pattern 100 includes a plurality of almond-shaped apertures 102 configured both circumferentially and longitudinally along the snare pattern 100. Each almond-shaped aperture includes curved members 104 shared by adjacent circumferential and longitudinal almond-shaped apertures 102.

The third snare pattern 100 additionally includes an elongate member 30 extending proximally from a pair of converging, undulating members 105 that lead to a first pair of circumferentially spaced, almond-shaped apertures 106 defined by curved members 104. Each of the first pair of circumferentially spaced, almond-shaped shaped apertures 106 are joined and share a portion of a sidewall 104 of two of four almond-shaped apertures defining a first ring 108 of almond-shaped apertures. In a presently preferred embodiment, a series of three additional nested rings 110 of almond-shaped apertures 102, though fewer or more are contemplated, complete a midsection 54 of the third snare pattern 100. Extending from terminal ends 112 of each almond-shaped aperture 102 of the distal most ring 110, is a distally directed extension 114.

In its manufactured form, the third snare pattern 100 has a midsection 54 that defines a generally tubular shape and a closed basket is formed by joining the terminal ends 112 of the most distal ring of apertures 110. Again, the terminal ends may be joined using soldering, laser welding, adhesive, shrink wrap, or by employing a coil configured about adjacent structure.

Figure 7:
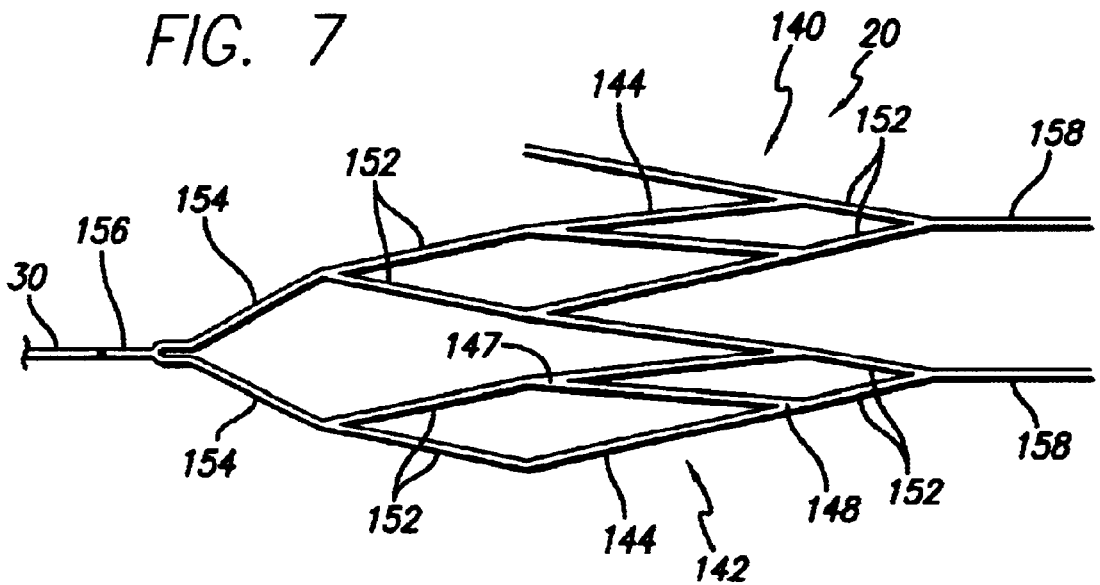
FIG. 7 is a plan view, depicting an unrolled pattern of a fifth embodiment of an intravascular snare of the present invention.

Additionally, the resultant structure includes a tapered opening to the tubular midsection 54 where the elongate member 30 extends proximally from a sidewall defining the tubular midsection 54 and where the elongate member 30 and distally directed members 114 are each parallel to a longitudinal access of the resultant snare device 20. The distally directed members 114 can be trimmed to a desired length. An additional feature of this embodiment (and FIG. 7 described below) is that the curved transitions from tab 53 to converging, undulating members 105 may enhance ease of retrieval of the device into a microcatheter.

Figure 6:
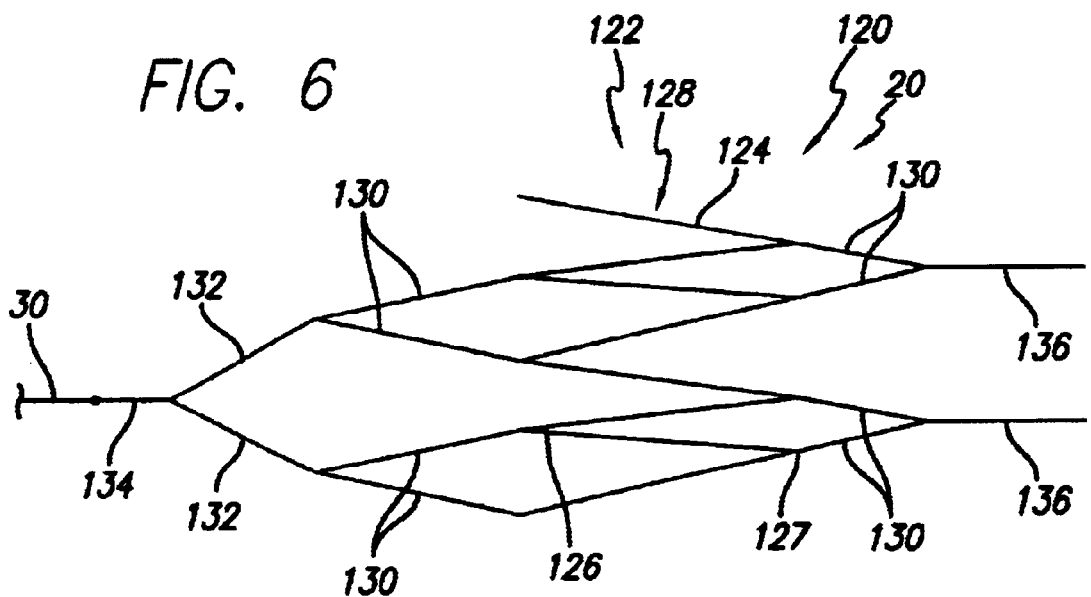
FIG. 6 is a plan view, depicting an unrolled pattern of a fourth embodiment of an intravascular snare of the present invention.

In a fourth embodiment (FIG. 6), the snare device 20 embodies a snare pattern 120 that includes a single conventional ring 122 defined by a continuous set of interconnected members 124. The interconnected members 124 are composed of straight struts that together define a central lumen in the manufactured form. The members 124 converge at ends thereof to form four proximal and distal crowns or vertices 126, 127 on each side of the ring 122. The ring 122 serves as a central body 128 of the snare device 20.

A single member 130 extends from each of the four crowns 126, 127 of the ring in both proximal and distal directions. Proximally, the four members 130 converge into two members 132, which again converge into a single member 134. This single proximal member 134 serves as a tab for attachment to the elongated member 30.

Extending from each of the members 130 projecting from the distal crowns 127 is a single distally directed extension 136. The distally directed extensions 136 can be configured to form an atraumatic tip as described herein below.

In a fifth embodiment (FIG. 7), the snare device 20 has a pattern 140 similar to that of the fourth embodiment. In particular, this pattern also includes a convoluted ring 142 defined of a continuous set of interconnected members 144. The interconnected members 144 are composed of straight sections that together form a central lumen 146 (see FIGS. 8–11) in the manufactured form. The members converge 25 at terminal ends thereof to form four proximal and distal crowns 147, 148 on each side of the ring 142, which serves as a central body 150 of the device 20. In this embodiment, however, alternative crowns 147, 148 at each end of the ring 142 are offset longitudinally from each other. Thus, every other interconnecting member 144 has a different length.

As with the fourth embodiment, a single member 152 extends from each of the four crowns 147, 148 in both proximal and distal directions. Further, the four members 152 connected to the proximal crowns 147 converge into two members 154, each of which again converge to form a proximal tab 156. At the distal end of the device 20, adjacent pairs of the single members 152 converge to a single extension 158. Again, the terminal ends 158 may be joined using soldering, laser welding, adhesive, shrink wrap, or by employing a coil configured about adjacent structure.

Figure 12:
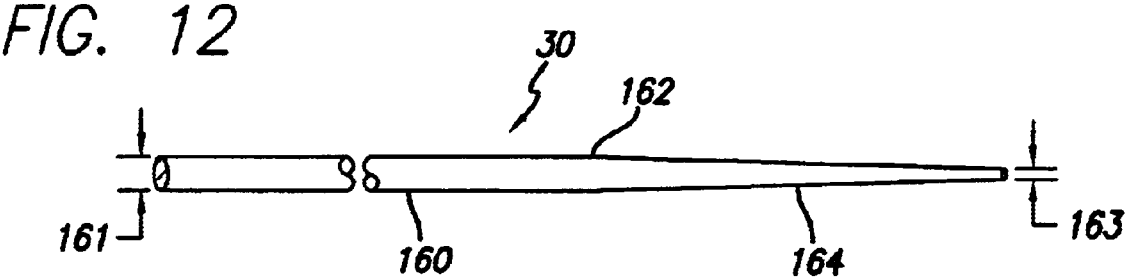
FIG. 12 is a side view, depicting an elongate member of the present invention.

Referring now to FIG. 12, there is shown one preferred embodiment of the elongated member 30 of the present invention. The member 30 embodies a gradual or step-tapered core comprising a proximal section of 304V stainless steel and a distal section of nitinol or an equivalent material for the intended purpose. A proximal portion 160 of the member 30 has a generally constant cross-sectional profile and a first diameter 161. At a transition point 162, the member 30 begins to taper in a gradual and consistent, alternatively in a step-tapered or a parabolic or other non-linear manner from the first diameter 161 to a second diameter 163 along a distal end portion 164.

Figure 13:
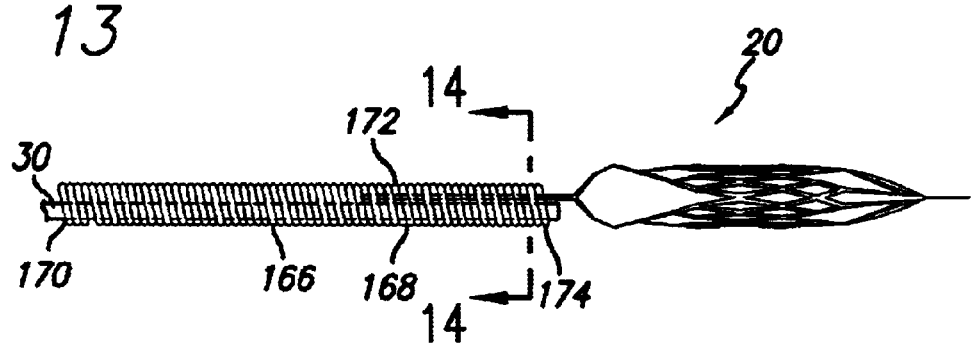
FIG. 13 is a side view, partially in cross-section, depicting a plurality of coils configured about a distal end portion of the elongate members in combination with a snare device of the present invention.
Figure 14:
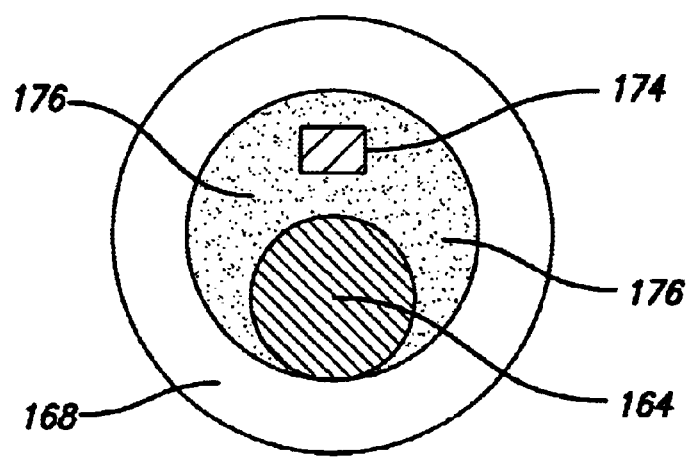
FIG. 14 is a cross-sectional view, taken along lines 14—14 depicting the assembly of FIG. 13.

As shown in FIGS. 13 and 14, a pair of longitudinally adjacent arranged coils 166, 168 are employed to attach a proximal tab 174 of a snare device 20 to the distal end portion 164 of the elongate member 30. The first, proximal coil 166 is contemplated to be composed of 304V stainless steel, the first coil being soldered to the elongate wire 30 near its tapered portion 170. The second coil 168 is contemplated to be comprised of a medical grade radiopaque wire, typically a platinum alloy such as about 90% platinum and 10% iridium alloy. This second coil 168, which serves as a radiopaque marker, is soldered to the elongate member 30 near a distal end portion 172 of the first coil 166. Alternatively, the second coil 168 is soldered to the first coil 166. A proximal tab 174 of the snare device 20 is contained within the second coil 168 and is soldered 176 to the elongate member 30.

Figure 15:
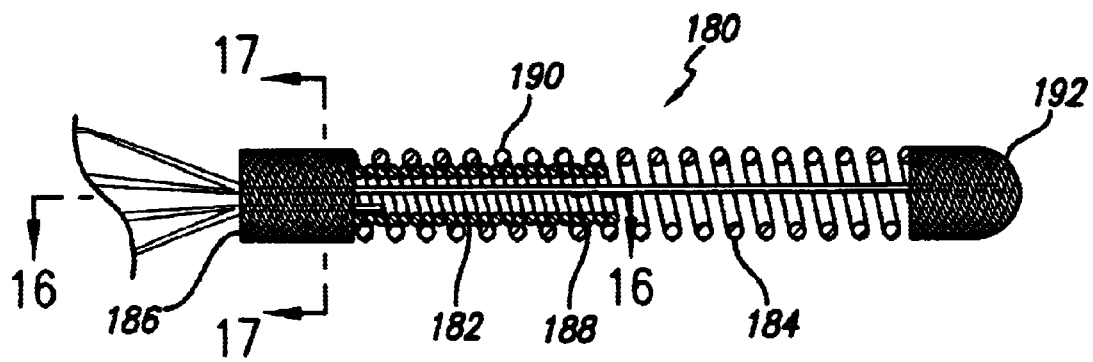
FIG. 15 is a side view, partially in cross-section, depicting a distal end portion of a tip of the snare device of the present invention.
Figure 16:
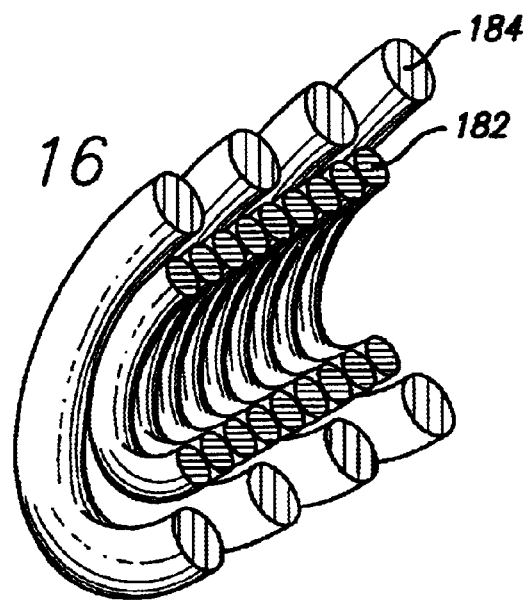
FIG. 16 is a cross-sectional view, taken along lines 16—16 of FIG. 15.
Figure 17:
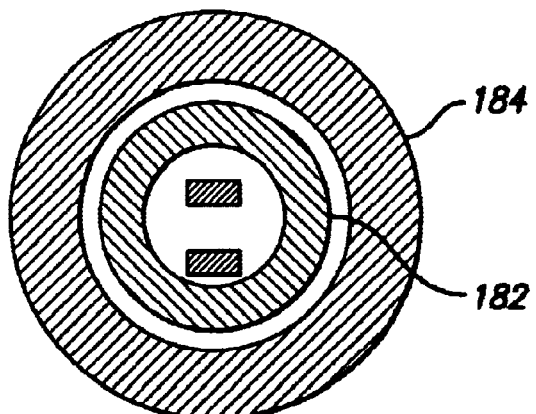
FIG. 17 is a cross-sectional view, taken along lines 17—17 of FIG. 15.

Turning now to FIGS. 15–17, one presently preferred embodiment of a distal tip portion 180 of the snare device 20 of the present invention is described. The distal tip portion 180 is comprised of two partially coaxial coils 182, 184, the combination of which retains the extensions projecting from the body of the snare device 20. The combination also provides a soft atraumatic tip with variable stiffness from softest distally to stiffer proximally. It is to be noted that a difference in relative length between the coils accomplishes changes in stiffness The inner coil 182 can be comprised of nitinol or equivalent material, and begins at a proximal location 186 and extends to a distal location 188. The nitinol inner coil 182 provides kink resistance as well as creates a smooth stiffness transition from the tip of the basket portion of the snare device 20. The outer coil 184 is coaxially configured about a distal portion 190 of the inner coil 182 and is preferably comprised of 90% platinum and 10% iridium alloy or an equivalent combination of materials. As such, the outer coil 184 can operate as a radiopaque marker.

The distal tip portion 180 further includes a rounded terminal end 192 that provides a blunt atraumatic surface. The terminal end 192 embodies a soldered joint which acts in retaining the helical configuration of the outer coil 184.

Figure 18:
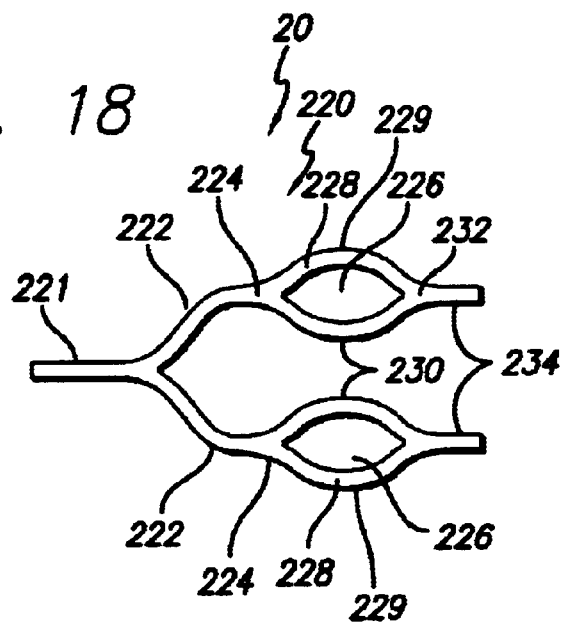
FIG. 18 is a plan view, depicting a portion of an unrolled pattern of yet other embodiment of an intravascular snare of the present invention.
Figure 19:
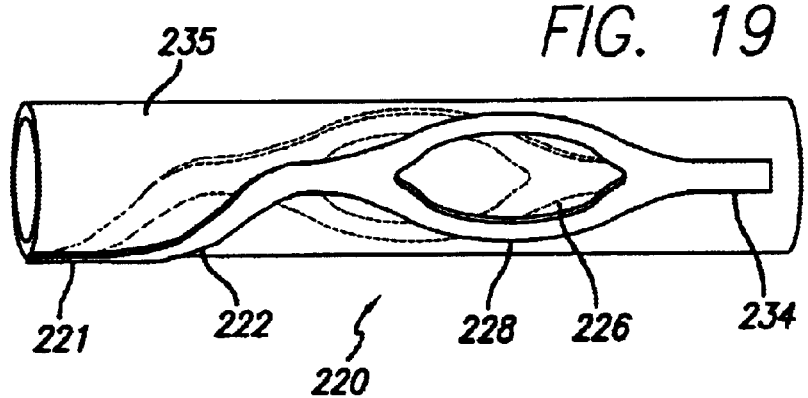
FIG. 19 is a perspective side view, depicting the pattern projected onto tube from which it may be cut to produce the snare device of FIG. 16.
Figure 20:
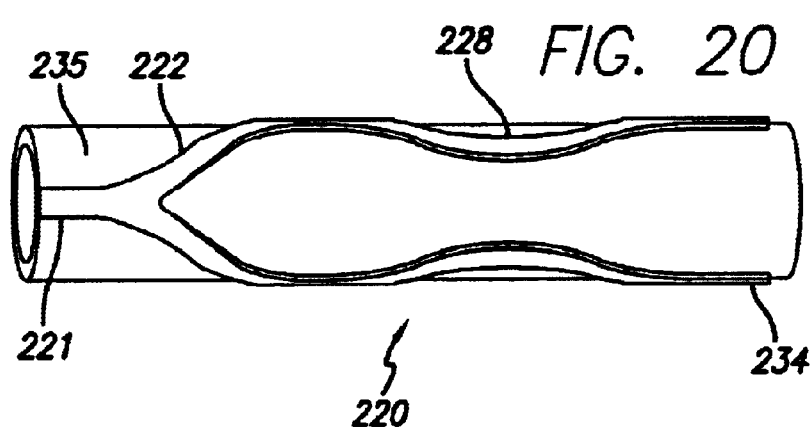
FIG. 20 is a perspective bottom view, depicting one step of a manufacturing process used to produce the snare device of FIG. 16.

With reference to FIGS. 18–20, a brief summary of the process used to manufacture the snare devices 20 of the present invention is provided, with a specific focus on a sixth embodiment of the present invention. As shown in FIG. 18, the sixth embodiment is relatively similar to a truncated third embodiment and defines a general stirrup-shaped pattern 220. This stirrup pattern 220 also includes a proximally directed tab 221 and a pair of diverging members 222 extending from the tab 221. Configured at each terminal end 224 of the diverging members 222 is a single almond-shaped shaped aperture 226 defined by curved members 228. The curved members 228 further include apices 229, 230 defining outer edges of the curved member 228. Moreover, joined to a distal end 232 of each almond-shaped opening 226 is a distally directed extension 234.

It is contemplated that the snare devices 20 of the present invention be cut from a tube 235 (FIGS. 19 and 20) using conventional means such as a laser. In particular, a specific pattern is programmed into the laser device and the laser is activated to cut the desired pattern into the tubular element 235. The excess tubular components are removed, thereby leaving a manufactured structure such as the stirrup snare pattern 220 shown in FIGS. 19 and 20, corresponding to the desired pattern. In a presently preferred embodiment, a super elastic material such as nitinol is a material of choice for the snare device 20. Thereafter, post-processing such as surface treatment, burr removal and deformation of the manufactured structure is performed. Heat treating is also performed for stress relief and sizing the device.

In particular, post-processing steps include taking an as-cut device and bead blast the device with aluminum oxide blasting media. The device is then inspected under a microscope for residual slag. If slag remains, the device is bead blasted again. Thereafter, the device is heat-treated in a molten salt bath without expanding. The device is subsequently heat-expanded in a molten salt bath mounted on a suitable size mandrel. After heat expansion, surface oxidation is removed in an aqua regia bath. When nitinol is the material of choice, the Nitinol can be etched with HF acid to desired softness or strut size. The device is then mounted on a guidewire.

In the case of the stirrup pattern 220, the post-processing may include deforming the pattern 220 and then joining together the distal end members 234 as well as adjacent apices 229, 230 for the purpose of achieving a closed basket for receiving debris found in vasculature. Being so configured, the pair of diverging members 222 define an opening to the resultant basket and the elongate member 30 extends from a sidewall defined by the pocket. Alternatively, distal end members 234 can be left apart and a basket attached to them as described below.

Figure 21:
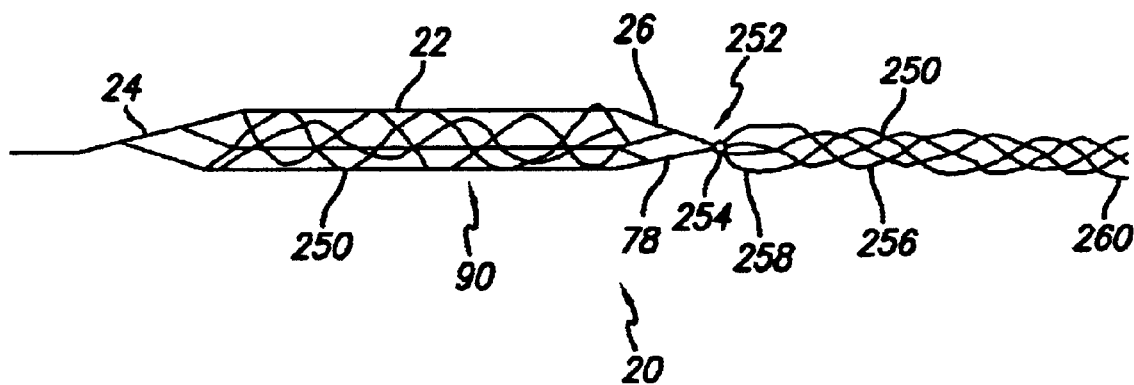
FIG. 21 is a side view, depicting an assembled snare device of FIG. 4 of the present invention including a braided structure for capturing emboli.

It is contemplated that certain circumstances may dictate other forms of a snare device 20. In particular, it is contemplated that a braided structure can be attached to a distal end portion of any of the previously described snare patterns. A braid can also be attached along the length of the body of the snare device. As shown in FIG. 21, one such braided structure 250 can be attached to, for example, a distal end portion 26, as well as the body snare pattern 90. In such a case, rather than terminating with distally directed members 78, the snare device 20 can include terminal apices 252 forming loops 254.

In one presently preferred embodiment, members 256 defining a first end 258 of the braided structure 250 can be attached to the loops 254 of the terminal apices 252 by conventional means. A second end 260 of the braided structure 250 can remain in an open configuration, or alternatively, members 256 defining the second end 260 can be joined to form a closed elongated tube.

The snare/braid assembly provides a number of advantages. In particular, such an assembly embodies additional volume for collecting debris from vasculature. Additionally, the braided structure includes sidewalls characterized by a higher density which can, in certain circumstances, be better suited for capturing relatively smaller debris found in vasculature.

Figure 22:
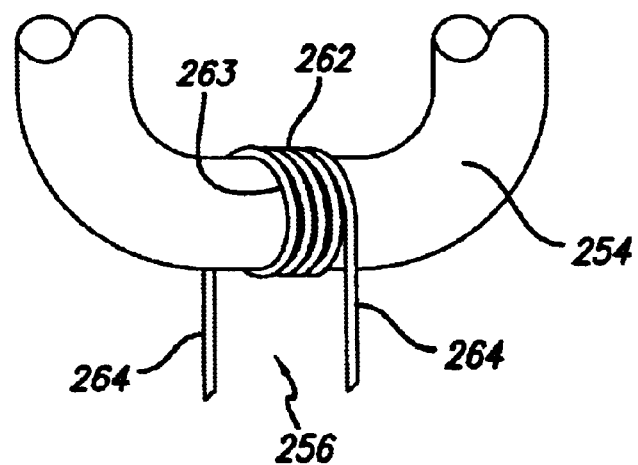
FIG. 22 is a perspective view, depicting one manner of attachment of the braided structure of FIG. 21 to a loop.

Turning to FIG. 22, it is important that the leading edges 262 of the connection between the braided structure 250 and the loops 254 formed in the distal end portions of a snare pattern be as atraumatic as possible. In one presently preferred embodiment, the members 250 defining a first end 258 of the braided structure 250 are configured into a two-legged coil 263 routed such that legs 264 of the coil extend from an outer surface of the loops 254 formed in the distal end portion 26. The coil is heat-set to enhance the connection to the snare pattern. It is also contemplated that single-leg coils (not shown) could additionally be used for attachment in the event forces required to unravel the single-leg coil are greater than the force necessary to deploy and retract the braided structure 250. An atraumatic leading end, however, remains an objective, as well as space considerations (i.e., low profile for packing into microcatheter).

Moreover, it is contemplated that biological materials can be applied to structures of the disclosed device either to facilitate lubricity for transversing a blockage or conversely to increase biological adhesion to the embolic or other material found in a patient. Also, biological material can be added for anti-thrombogenicity.

The snare devices of the present invention compared to prior art loop snares each provide improved radial opening since in an expanded state, the elongate member 30 is positioned substantially out of the flow path. Additionally, the device embodies improved resistance to radial loads compared to prior art loop snares. Moreover, since less deformation is required to produce a desired snare pattern, in that, angles between members are provided by laser cutting rather than from local deformations, for example, there is improved stress distribution along the snare devices of the present invention compared to prior art loop snares. Additionally, a greater reduction in radial profile can be achieved without sacrificing performance and in particular, the device can be used in conjunction with conventional catheters and in some instances microcatheters. As such, the snare devices 20 of the present invention can be passed through narrow and tortuous vasculature. The applications of the present invention are more widespread than that of conventional snare devices because of greater retrieval characteristics while retaining the deliverability characteristics.

The above described invention is principally conceived to be operational for use in engaging for the purpose of displacing and/or removing material either foreign or native to the body, including partial or complete obstructions embolic and/or thrombotic in nature, from intraluminal or extraluminal spaces of the body including but not limited to intravascular and/or intra-arterial regions of the neurovasculature, as well as tubings, stents, or other objects that may or may not be internal to the body. The purpose of the device is to restore functionality of the luminal space or systems dependent on the particular luminal space or as a method of producing any desired effect associated with the removal or displacement of undesirable material.

The intended delivery of the disclosed invention is by means of a commercially available catheter selected to its ability to access the desired location of engagement. The invention may be optimized for specific locations or uses by means of sizing the individual elements in the design and/or the overall dimensions, as well as selection of materials, mesh configuration, number and relative geometry of component members to meet the requirements of the operational space. Optimizations may include tabs protruding from the sides of members to increase coverage of the open areas between members, offsetting vertices of joints to increase packing efficiency, or providing unconnected distal curved path. There may additionally be variations of the dimensions of length, thickness, and width of distal and proximal tabs for joining basket with delivery wire and distal tip to provide smooth stiffness transitions from tip to basket and basket to delivery wire. Such optimizations are means of adjusting operational attributes including: flexibility, applied circumferential force, engagement effectiveness, deliverability and traversal through tortuous vasculature, and volume of material to be engaged.

Alternate or additional materials for the basket portion of the device may include a thermoset, elastomer, thermoplastic constituents such as nylon, or other metal either pure or alloyed, as well as composite materials such as a combination of glass, aramid, or carbon in a binding matrix. Human or non-human biological materials may also be used. A secondary mesh of the same or dissimilar material may be added to the basket. The wire portion of the device can alternatively be made from a single metal or combination of metals for kink resistance and high flexibility. Either or both components may be tapered to give a transition in stiffness that is appropriate for the vessel in which the invention is to be delivered. The distal tip of the device may incorporate concentric coils made of nitinol, stainless steel, or other metal or plastic to provide a soft flexible atraumatic end.

An alternate method of manufacture of the basket portion of the device may be etching, or metal or injection molding. Furthermore, the device may employ any combination of coatings, agents, or features including those of that result from material addition or subtraction to create grooves, bumps, three dimensional patterns, and textures on inner and/or outer surfaces or any combination thereof to promote desired properties such as adherence of materials to be engaged, radiopacity, and low friction between the device and the vessel wall or microcatheter lumen.

As stated, in one embodiment of the present invention, a secondary material can be added to a basket structure. Such a device is contemplated to be employed as an embolic protection device. In use, the embolic protection device is deployed downstream of an interventional treatment site and is configured to collect from vasculature any unwanted debris that results from the procedure.

Figure 23:
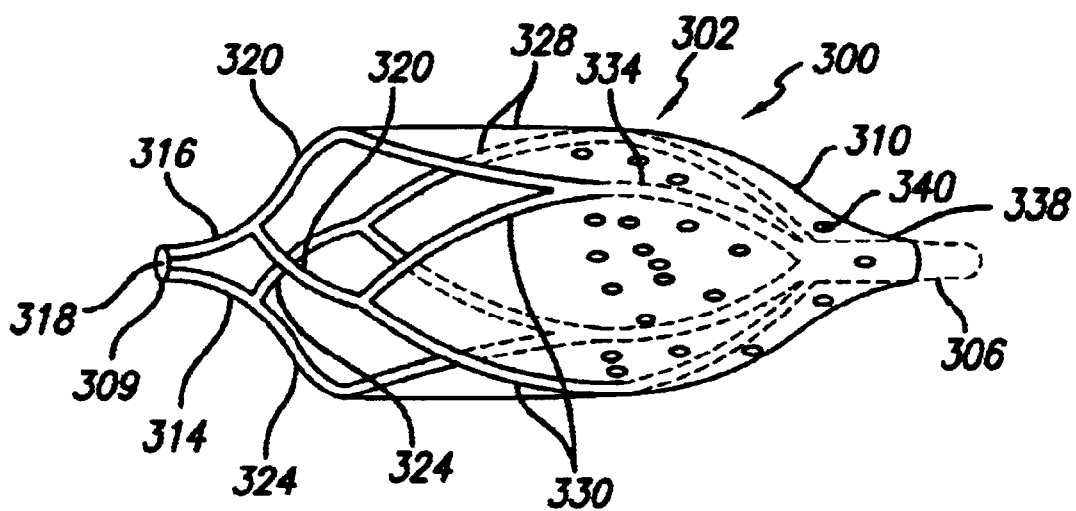
FIG. 23 is a perspective view, depicting an embodiment of a protection device of the present invention.

With reference to FIG. 23, there is shown one embodiment of an embolic protection device 300. The embodiment depicted includes a cage or basket portion 302 having a proximal end 304 and a distal end 306, and a filter portion 310. The embolic protection device 300 is contemplated to be used in combination with a generally tubular catheter or microcatheter which is configured to receive the embolic protection device 300 in a collapsed or compressed configuration and to be translated longitudinally with respect to the embolic protection device 300 to accomplish delivery and withdrawal of the same within vasculature. The cage 302 can be made from nitinol or other acceptable material and the filter 310 can embody a flexible biological or non-biological membrane, such as a polymer or other suitable membranous material. Further, the cage 302 can be manufactured from a tube using a laser. The rib members can have a thickness on the order of 0.007 inches and a width around 0.003 inches. Further, the ring members can be 0.0035–0.006 inches wide but smaller and larger dimensions are contemplated and can be up to 0.003 inches thick or more.

In one aspect, the proximal end portion 304 of the embolic protection device 300 includes a collapsible body or cage 302 defined by a pair of rib members 314, 316 extending distally from a longitudinal extending member or guide wire 318. Relative movement between the catheter used to deliver the protection device 300 within vasculature may be accomplished by applying pushing or pulling forces on the longitudinally extending member 318. Each rib member 314, 316 branches into a pair of proximal ring members 320, 324, each of which, in turn, branch into pairs of distal ring members 328, 330. Adjacent pairs of distal ring members 328,330 converge into single members 334, each of which again converge to define the distal end portion 306 of the body or cage.

The filter 310 is attached to the distal ring members 328 and is configured to span the space defined by the branching ring members 328. The filter 310 can be configured to follow the profile defined by the cage. Alternatively, as is shown in FIG. 23, the filter 310 can assume a wind sock arrangement wherein a proximal portion of the filter 310 is attached to the distal members 328 but separates from the cage at a point where the distal members converge. The distal portion 338 of the filter 310 tapers and is attached by glue or other equivalent conventional means or devices to the protection device 300. The filter 310 further includes micropores or other openings 340 formed therein. The openings 340 are designed to permit the passage of blood through the filter 310 while preventing the passage of debris.

Figure 24:
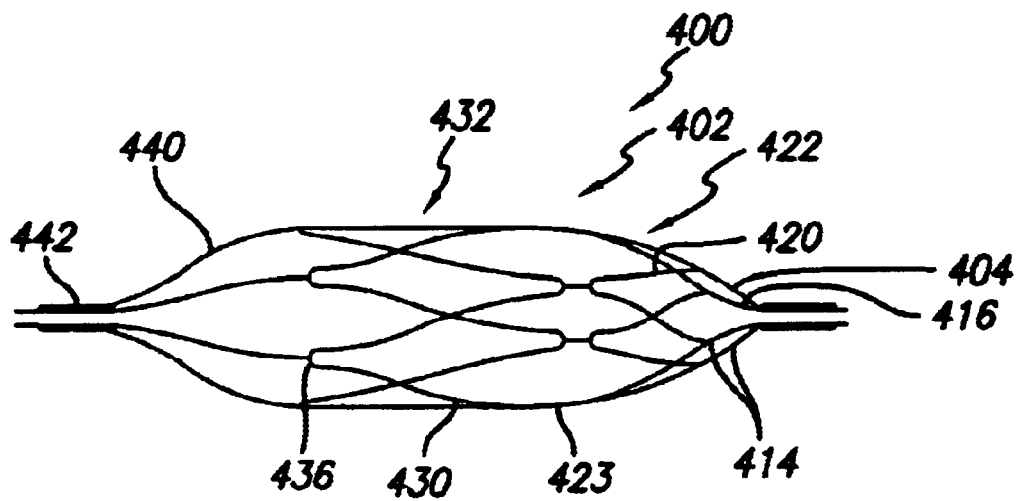
FIG. 24 is a perspective view, depicting a second embodiment of a protection device of the present invention.

In other embodiments of the protection device of the present invention, the cage can include additional rib and ring members. As shown in FIG. 24, a protection device 400 can include a collapsible cage 402 having a proximal end portion 404 defined by two pairs of rib members 414, 416, each of which extend distally and branch into pairs of proximal ring members 420. The proximal ring members 420 converge and define a first ring 422. At a point where adjacent pairs of ring members 420 converge, there is a plurality of circumferentially arranged linking members 423, each of which branch into pairs of distal ring members 430, adjacent pairs of which also converge and collectively, define a second ring 432. Extending from peaks 436 formed at a distal end of the second ring 432, are single longitudinally extending members 440 which converge and define a distal end portion 442 of the protection device 400. In one embodiment, the members defining the second ring 432 are longer than the members defining the first ring 422.

Although various sizes of the cage 402 are contemplated, in one aspect, the cage 402 has a mid-section having an outer diameter of approximately 4.5 millimeters. As stated, the cage 402 can be cut from a tube. In order to form a cage 402 having an outer diameter of 4.5 millimeters, for example, the cut tube can be initially expanded and shape set by first employing a pair of 2 millimeter balls at the proximal end portion 404 followed by a pair of 4.5 millimeter spheres placed within a mid-section of the device. Other sized cages can of course be formed using a system of larger or smaller sized spheres.

Figure 25:
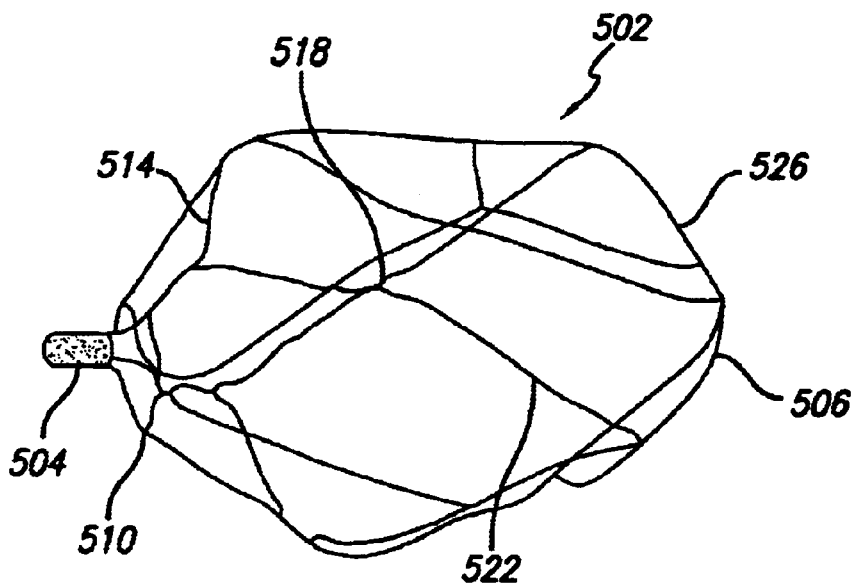
FIG. 25 is a perspective view, depicting a third embodiment of a protection device of the present invention.

Turning to FIG. 25, there is shown yet another embodiment of a cage 502 having a proximal end portion 504 and a distal end portion 506. In this embodiment, four diverging ribs 510 extend distally, each branching into a pair of ring members 514. Each of the ring members 514, in turn, converge within an adjacent ring member 514 to define a link 518. Extending distally from each link 518 are a pair of second ring members 522, each of which also converge into distally extending, terminal members 526. The terminal members 526 are joined to define the distal end 506 of the cage 502. Although various sizes are contemplated, in one aspect, the resulting cage 502 has a mid-section defining a 6.7 millimeter outer diameter.

Each of the cages 402, 502 depicted in the figures are contemplated to include a filter. As before, the filter can follow the profile of the cage 402, 502 or can define a wind sock configuration.

Figure 26:
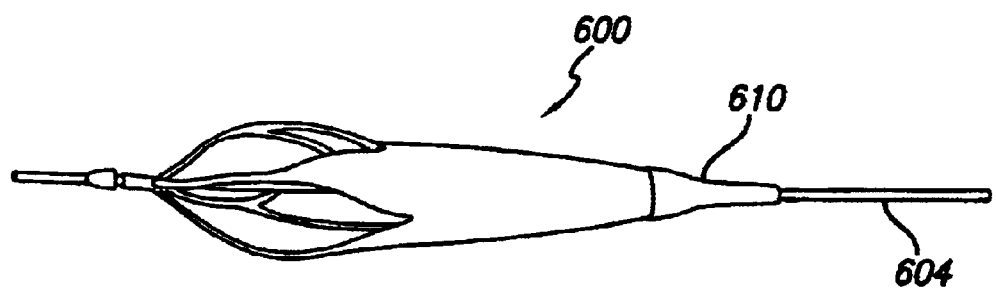
FIG. 26 is a perspective view, depicting a fourth embodiment of a protection device equipped with a distal tapered section.
Figure 27:
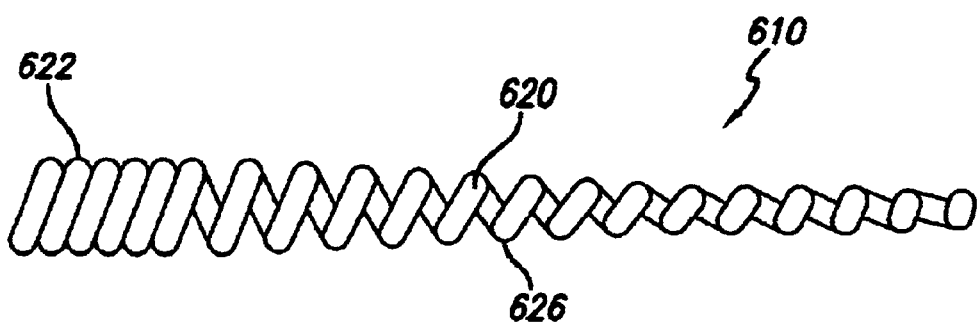
FIG. 27 is an enlarged view, depicting one embodiment of a distal tapered section.

A protection device 600 of the present invention can additionally include a distal end portion 604 including a distal tapered section 610 (see FIG. 26). In one embodiment, as shown in FIG. 27, the distal tapered section 610 can be embodied in a coil having a proximal portion 622 and a distal portion 624 and a profile that tapers from the proximal to distal portions. In one aspect, the coil 620 has tightly arranged coil sections at the proximal end 622 and spaced coils along a mid-section 626 and distal portion 624. Moreover, it is contemplated that the space in between the coils be varied such that there are larger spaces between coil sections at the distal portion 624 as compared to the mid-section 620. Such a design is intended to provide the protection device with a desired flexibility.

Figure 28:
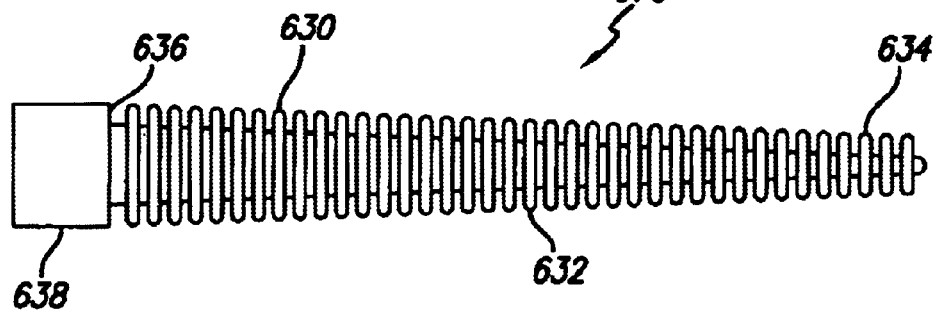
FIG. 28 is an enlarged view, depicting a second embodiment of a distal tapered section.

In another embodiment (FIG. 28), the distal tapered section 610 can be embodied in a tapered structure having ribs 630 extending generally perpendicularly from a longitudinal component 632. The ribs 630 can embody discrete sections or can be defined by a helix arranged along the distal tapered section 610. The spacing between adjacent ribs can be varied and in one aspect, such spacing can be greater at a distal end 634 of the distal tapered section 610 than at a proximal end 636 thereof. Additionally, the proximal end 636 of the distal tapered section 610 further includes an enlarged diameter shoulder 638. The distal tapered section 610 is also contemplated to include an internal bore adapted for receiving structure defining a distal end of the protection device of the present invention and for fixedly attaching the distal tapered section to the protection device.

Figure 29:
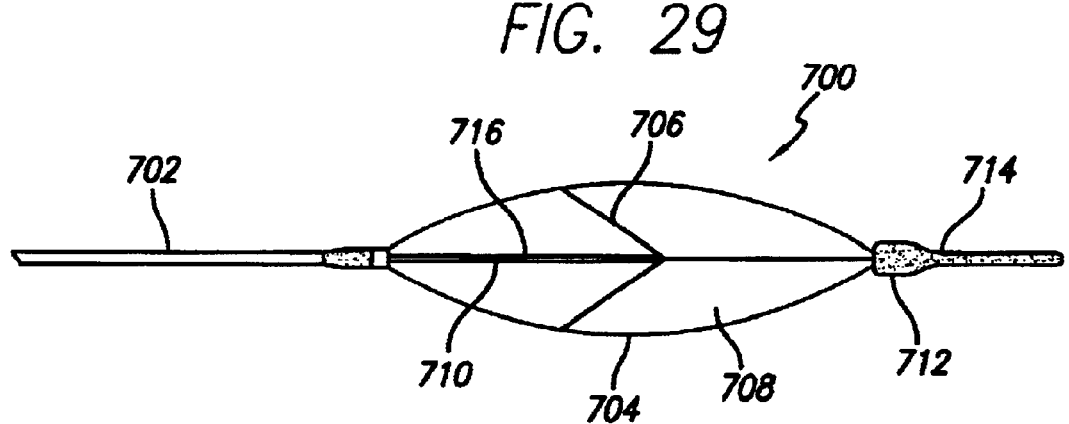
FIG. 29 is a perspective view of a fifth embodiment of a protection device.
Figure 30:
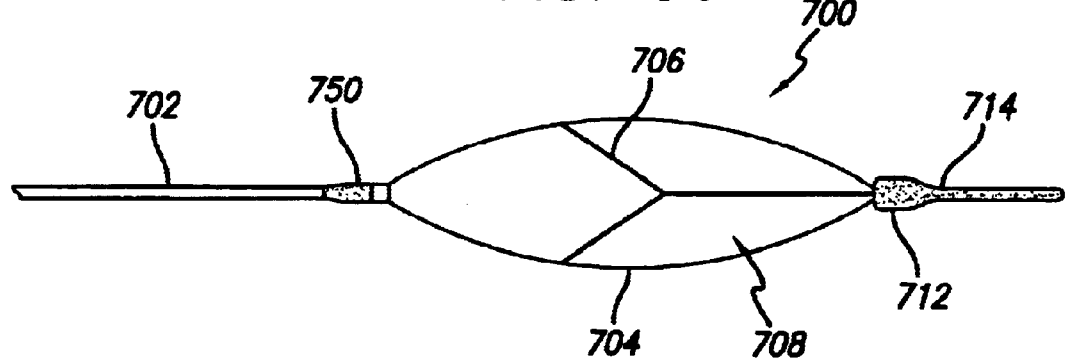
FIG. 30 is a perspective view of a sixth embodiment of a protection device.

Turning now to FIGS. 29 and 30, there are depicted protection devices configured to enhance stiffness transition and provide desired flexibility. In one embodiment, the protection device 700 (FIG. 29) is attached to a guide wire or other elongate member 702. The protection device 700 includes a body 704 defined by struts 706 and includes filter material 708 spanning selected struts 706. A support member 710 extends from the point of attachment of the body 704 to the guide wire 702 through an interior defined by the body 704 and terminates at a terminal end 712 of the protection device 700. The terminal end 712 is further provided with a distal tapered section 714. In the depicted embodiments, it is contemplated that the support member 710 include a reduced profile section 716 which could be formed by grinding down a core of the device or can be an additional plastic member made from polymide or other plastic material.

Alternatively, the protection device 700 can completely lack the support member (see FIG. 30) and can further include a pivoting structure 750 configured at the connection between the cage of the protection device 700 and the guide wire 702. Such a pivot 750 can be defined by a collar having an internal bore that receives the guide wire 702 which is flanged or includes an enlarged diameter structure at its terminal end, the same being held within the collar in a manner to permit rotation of the guide wire 702 with respect to the body 704 of the protection device 700.

Protection device designs incorporating structure permitting independent rotation of a guide wire or include a reduced diameter support member or equivalent structure, as stated, have enhanced stiffness transition along the length of the device. Such devices also embody structure having a built-in natural bending point and consequently, are better suited for deployment at bends or within eccentric anatomy. Further, such structure acts like a shock absorber to reduce movement of the basket or cage of the protection device relative to the core or guide wire. Moreover, by lacking a support member or by incorporating a reduced profile support member, the protection device has a reduced profile when compressed. Furthermore, protection devices including structure facilitating relative axial rotation or pivoting between structural components provide a mechanism to prevent the core wire or guide wire from inadvertently rotating the protection device cage or for that matter, from becoming entangled with the cage during advancement within vasculature.

The body of a protection device can also be equipped with structure aimed at absorbing core or guide wire twisting and movement. As shown on FIG. 31, a protection device 800 can be configured to include a proximal end portion 802 including a plurality of rib members 803, each of which are configured into a radially directed open loop 804. A distal end of each rib member 802 is attached to a ring 806 to define a reduced diameter segment. A plurality of generally longitudinally directed member 808 extend distally from the ring 806 and branch into a pair of members 810 defining a second ring structure 812. Further, a member ring or filter 820 can be attached to the cage of the protection device 800 at the second ring structure 812. As with the previous devices, such a protection device can be used in combination with a generally tubular delivery catheter for receiving the protection device in a collapsed configuration as well as to accomplish delivery at a repair site.

It is to be recognized that the loop section 804 of the protection device assembly 800 operates to absorb core or guide wire movement and bending to retain wall apposition. With conventional protection devices, movement of the core or guide wire results in forces being directly transmitted to the body or cage of the protection device which may cause caged distortion and loss in wall apposition. The loop structure 804 substantially reduces the transmitted forces to the cage that makes contact with a vessel wall and provides substantial lateral flexibility. The ring member 806 provides the device with stability. However, it is also contemplated that a protection device can lack the ring member 806 or further include a spring cut from the cage material.

In yet another alternative embodiment (FIG. 32), the protection device 900 of the present invention can further include a cage body with a mid-section 904 including two single leg, bendable articulations 906. Such structure is intended to improve flexibility and to facilitate keeping a distal portion 908 of the cage open when deployed at a bend in vasculature 920 (see FIG. 33).

It is to be recognized that any of the disclosed embodiments can include the described substructures that absorbs or modifies forces translated by the guide or core wire. Likewise, any of the devices disclosed can embody the obturators or distal tips disclosed herein or for that matter, a filter membrane.

The devices of the present invention are deliverable to remote regions of the neurovasculature or other lumen spaces by gaining access through the use of a guidewire and a catheter in the vasculature and subsequent deployment of the invention through the lumen of the microcatheter. In a vessel in which flow is impeded or obstructed by material and/or objects including those formed by the body such as blood clot, the device is deployed by withdrawing the microcatheter relative to the wire. Engagement occurs as the system composed of the invention and microcatheter is pulled into the material. Alternatively, emboli or other unwanted debris or material created during an interventional procedure can be collected by the disclosed devices employing a passive approach whereby the device is held steady in vasculature and the debris is collected from blood flowing through the device. After the unwanted material has been engaged or collected, removal of the material is accomplished by withdrawing the system into a guide catheter lumen through which the microcatheter is passed with or without simultaneously pulling fluid through the guide lumen.

Thus, it will be apparent from the foregoing that, while particular forms of the invention have been illustrated and described, various modifications can be made without the parting from the spirit and scope of the invention. Accordingly, it is not intended that the invention be limited, except as by the appended claims.

What is claimed is:

1. An intravascular device for use in a body lumen, comprising:

an elongate member having a first end portion and a second end portion, the first end portion configured to extend exterior of the body lumen; and a body attached to the second end portion of the elongate member, the body being configured for deployment within the body lumen and including a substructure that absorbs forces applied to the body by the elongate member and a material collection body section, the substructure being separate and distant and longitudinally removed from the material collection body section to thereby substantially isolate the material collection body section and absorb bending and movement of the elongate member.

2. The device of claim 1, wherein the body has a proximal portion, a midsection and a distal portion, the proximal portion being attached to the elongate member.

3. The device of claim 2, the substructure further comprising a loop structure configured at the proximal portion of the body.

4. The device of claim 3, wherein the loop structure is defined by a plurality of rib members.

5. The device of claim 4, the proximal portion of the body further comprising a ring member attached to the loop structure.

6. The device of claim 2, the distal end portion of the body including a distal tapered section.

7. The device of claim 1, further comprising a filter extending along a length of the body, the filter including pores.

* * * * *

UNITED STATES PATENT AND TRADEMARK OFFICE
CERTIFICATE OF CORRECTION

PATENT NO. : 6,660,021 B1
DATED : December 9, 2003
INVENTOR(S) : Olin Palmer et al.

It is certified that error appears in the above-identified patent and that said Letters Patent is hereby corrected as shown below:

Column 3,
Line 53, should be part of paragraph directly preceding it.

Column 4,
Line 24, after "vasculature" insert -- and --.

Column 15,
Line 57, delete "0.007", and insert -- 0.003 --.

Column 16,
Line 11, after "328" insert -- , 330 --.
Line 41, after "442" insert -- Alternatively, ring 432 could be shorter or Of equal length to ring 422 --.

Signed and Sealed this

Twenty-seventh Day of July, 2004

JON W. DUDAS
*Acting Director of the United States Patent and Trademark Office*

UNITED STATES PATENT AND TRADEMARK OFFICE
CERTIFICATE OF CORRECTION

PATENT NO.    : 6,660,021 B1
DATED         : December 9, 2003
INVENTOR(S)   : Olin Palmer et al.

It is certified that error appears in the above-identified patent and that said Letters Patent is hereby corrected as shown below:

Column 3,
Line 53, should be part of paragraph directly preceding it.

Column 4,
Line 24, after "vasculature" insert -- and --.

Column 15,
Line 57, delete "0.007", and insert -- 0.003 --.

Column 16,
Line 11, after "328" insert -- , 330 --.
Line 15, after "328" insert -- , 330 --.
Line 41, after "442" insert -- Alternatively, ring 432 could be shorter or of equal length to ring 422. --.

Signed and Sealed this

Sixteenth Day of November, 2004

JON W. DUDAS
*Director of the United States Patent and Trademark Office*

UNITED STATES PATENT AND TRADEMARK OFFICE
CERTIFICATE OF CORRECTION

PATENT NO.    : 6,660,021 B1
DATED         : December 9, 2003
INVENTOR(S)   : Olin Palmer et al.

It is certified that error appears in the above-identified patent and that said Letters Patent is hereby corrected as shown below:

Column 3,
Line 53, should be part of paragraph directly preceding it.

Column 4,
Line 24, after "vasculature" insert -- and --.

Column 15,
Line 57, delete "0.007", and insert -- 0.003 --.
Line 58, delete "0.003", and insert -- 0.007 --.

Column 16,
Line 11, after "328" insert -- , 330 --.
Line 15, after "328" insert -- , 330 --.
Line 41, after "442" insert -- Alternatively, ring 432 could be shorter or of equal length to ring 422. --.

This certificate supersedes Certificate of Correction issued November 16, 2004.

Signed and Sealed this

Third Day of May, 2005

JON W. DUDAS
*Director of the United States Patent and Trademark Office*